US00PP36743P2

(12) United States Plant Patent
Gmitter, Jr.

(10) Patent No.: US PP36,743 P2
(45) Date of Patent: Jun. 17, 2025

(54) ***CITRUS* PLANT NAMED 'UF 1859'**

(50) Latin Name: ***Citrus* sp.**
Varietal Denomination: UF 1859

(71) Applicant: Florida Foundation Seed Producers, Inc., Marianna, FL (US)

(72) Inventor: Frederick Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/735,085

(22) Filed: Jun. 5, 2024

Related U.S. Application Data

(60) Provisional application No. 63/510,486, filed on Jun. 27, 2023.

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./201, 202
See application file for complete search history.

(56) References Cited

U.S. PATENT DOCUMENTS

PP21,356 P3 10/2010 Gmitter, Jr. et al.
PP21,535 P2 11/2010 Grosser et al.

OTHER PUBLICATIONS https://www.fdacs.gov. "Citrus Budwood—Annual Report—2020-2021" (Retrieved from the Internet on Oct. 10, 2024.).*

* cited by examiner

*Primary Examiner* — Susan McCormick Ewoldt
(74) *Attorney, Agent, or Firm* — Koenig IP Works, PLLC; Katherine Koenig

(57) ABSTRACT

A new and distinct seedless, sweet orange-mandarin hybrid, with distinctive shape and color, that can be harvested through a season extending for at least three months. The new citrus cultivar, named 'UF 1859', also appears to be more tolerant to HLB than most mandarin varieties, showing standard leaf, foliage, and fruit morphology and dense foliage despite being CLas positive.

22 Drawing Sheets

Genus and species: *Citrus* sp.
Cultivar denomination: 'UF 1859'.

ACKNOWLEDGEMENT OF FEDERAL RESEARCH SUPPORT

N/A.

BACKGROUND OF THE NEW CULTIVAR

The present invention relates to a new and distinct cultivar of *Citrus*, botanically known as *Citrus* sp., and hereinafter referred to by the name of 'UF 1859'. The new cultivar 'UF 1859' arose from a cross of 'LB8-9' mandarin hybrid x ('Nova' tangelo+'Succari' sweet orange, a somatic hybrid of two unpatented *Citrus* cultivars). The former (female parent), 'LB8-9', is a patented cultivar (U.S. Plant Pat. No. 21,356) and the latter (male parent) is an unreleased and proprietary (unpatented) breeding parent of a *Citrus* breeding program. The cross was made in 2001 in an experimental orchard in Lake Alfred, Florida. Embryo rescue was performed to generate a viable shoot that was micrografted onto a 'Carrizo' citrange (unpatented) seedling, and the resulting young tree was planted in Lake Alfred in Spring 2003. The tree was selected in 2018 as one producing fruit with very desirable characteristics. Topworked trees in Lake Alfred, Florida, and in Polk County, Florida, have produced fruit since that time that are true to type.

SUMMARY OF THE INVENTION

The new *Citrus* cultivar 'UF 1859' has not been observed under all possible environmental conditions. The phenotype of the new cultivar may vary with variations in environment and cultural practices such as temperature, light intensity, fertilization, irrigation, and application of plant growth regulators without any change in genotype.

This cultivar provides annual crops of well-colored fruit that are seedless, and in general resemble sweet orange in size and shape with some notable differences, such as deeper external orange color in Florida growing conditions and a more aromatic flavor profile sometimes described as "floral with tropical notes." The fruits begin to mature in mid-late November in central Florida, but can be harvested until late January, improving in internal and external color as well as flavor over that time. The external color of fruit is a much deeper orange at maturity than typical sweet oranges. Likewise, the internal color of fruit is a deep orange.

The juice of the new cultivar 'UF 1859' is sweet though balanced with acidity, described as more floral, aromatic, and tropical than sweet orange. Juice Brix values measured in January 2021 were averaging 14 and acidity averaged 0.8%, giving a Brix: acidity ratio of about 17.5. Juice color scores are 37 and above. The attractiveness of the fruit and their resemblance to true sweet oranges, albeit with substantially deeper external color and smoother rind, make fruit of 'UF 1859' particularly suitable for the fresh market. Additionally, the abundance of juice and high Brix: acidity ratio also make fruit of 'UF 1859' suitable for the processed juice market.

The present botanical description is that of the cultivar grown as a 17-year-old tree on 'Carrizo' citrange rootstock in Lake Alfred, Florida. At the time of evaluation, the tree had been CLas+ (that is, positive for *Candidatus* Liberibacter asiatus) for at least ten years, and the juice values far exceeded state average values for typical sweet orange juice during this same time. The original source tree was grown in an orchard devastated by Huanglongbing (*Citrus* greening disease), and it was selected based on tree health and for the quality of the fruit produced, in spite of the disease pressure.

DESCRIPTION OF THE FIGURES

The accompanying photographs (as shown in FIGS. 1A-6B) illustrate the overall appearance of the new *Citrus* cultivar 'UF 1859'. These photographs show the colors as true as can be reasonably obtained in colored reproductions of this type. Colors in the photographs may differ slightly from the color values cited in the detailed botanical description, which accurately describe the colors of the new *Citrus* cultivar.

DETAILED BOTANICAL DESCRIPTION OF THE CULTIVAR

Figure 1A:
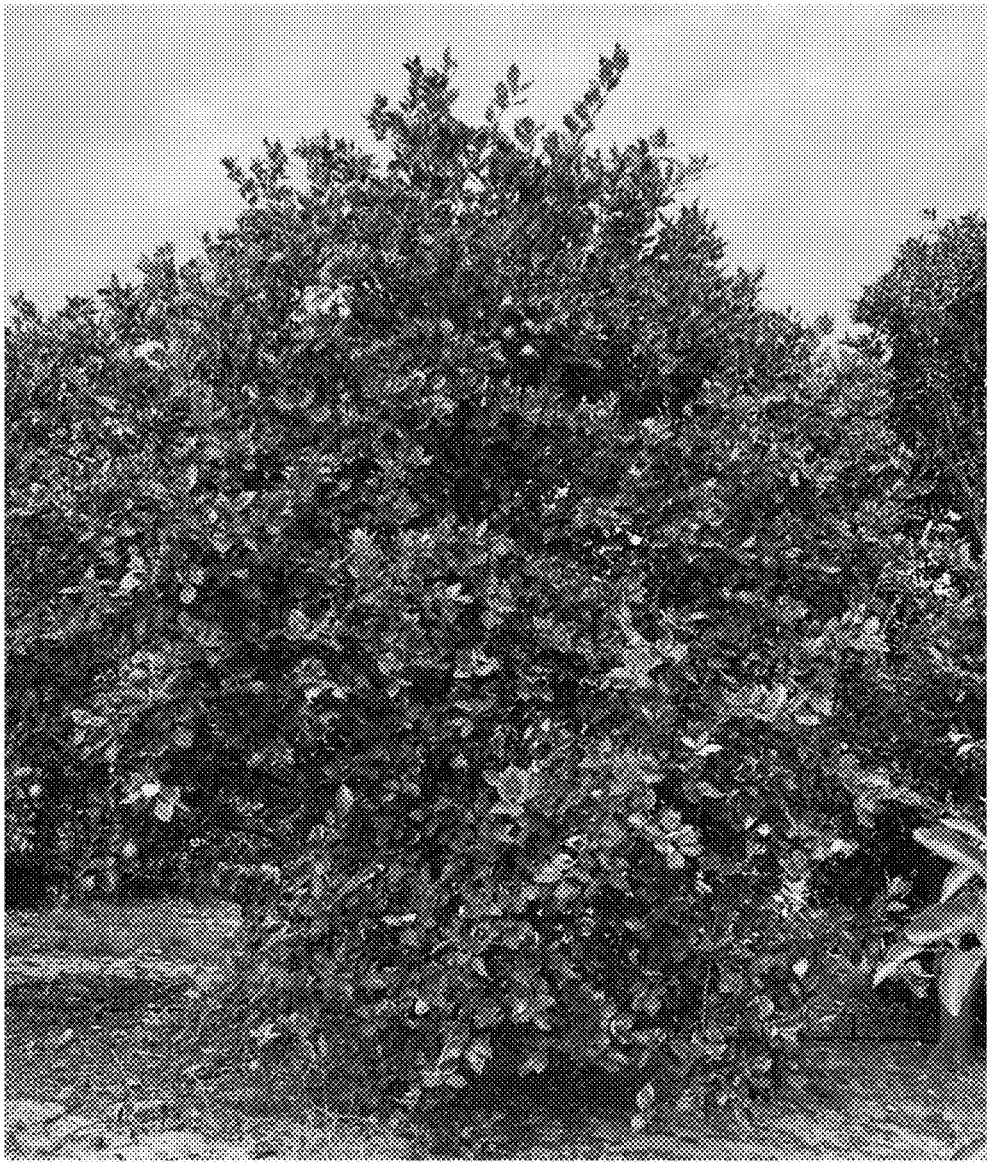
FIG. 1A is a photograph of a tree of the new *Citrus* cultivar 'UF 1859' showing the overall growth habit.
Figure 1B:
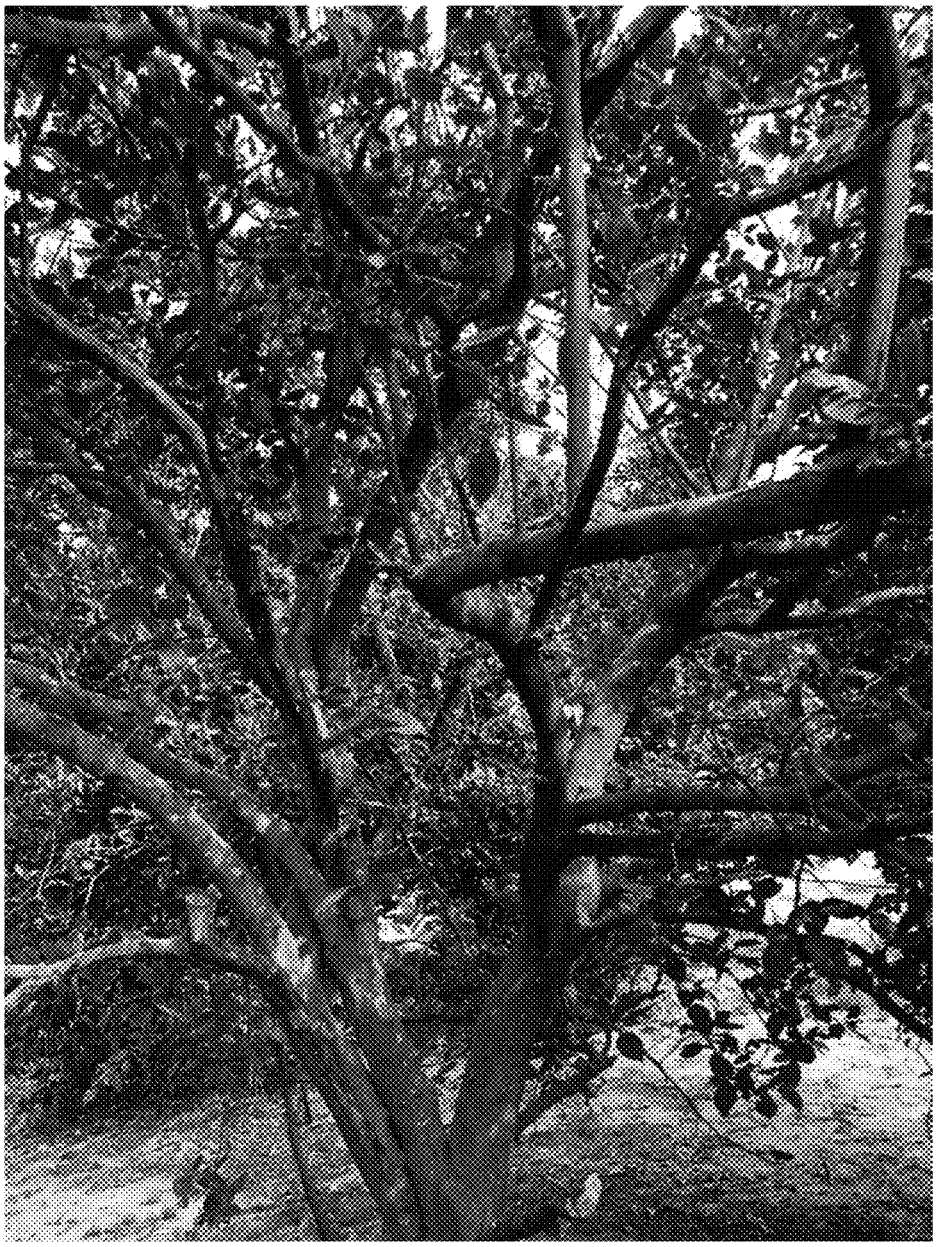
FIG. 1B is a photograph of a tree of the new *Citrus* cultivar showing the overall growth habit, including branching.
Figure 1C:
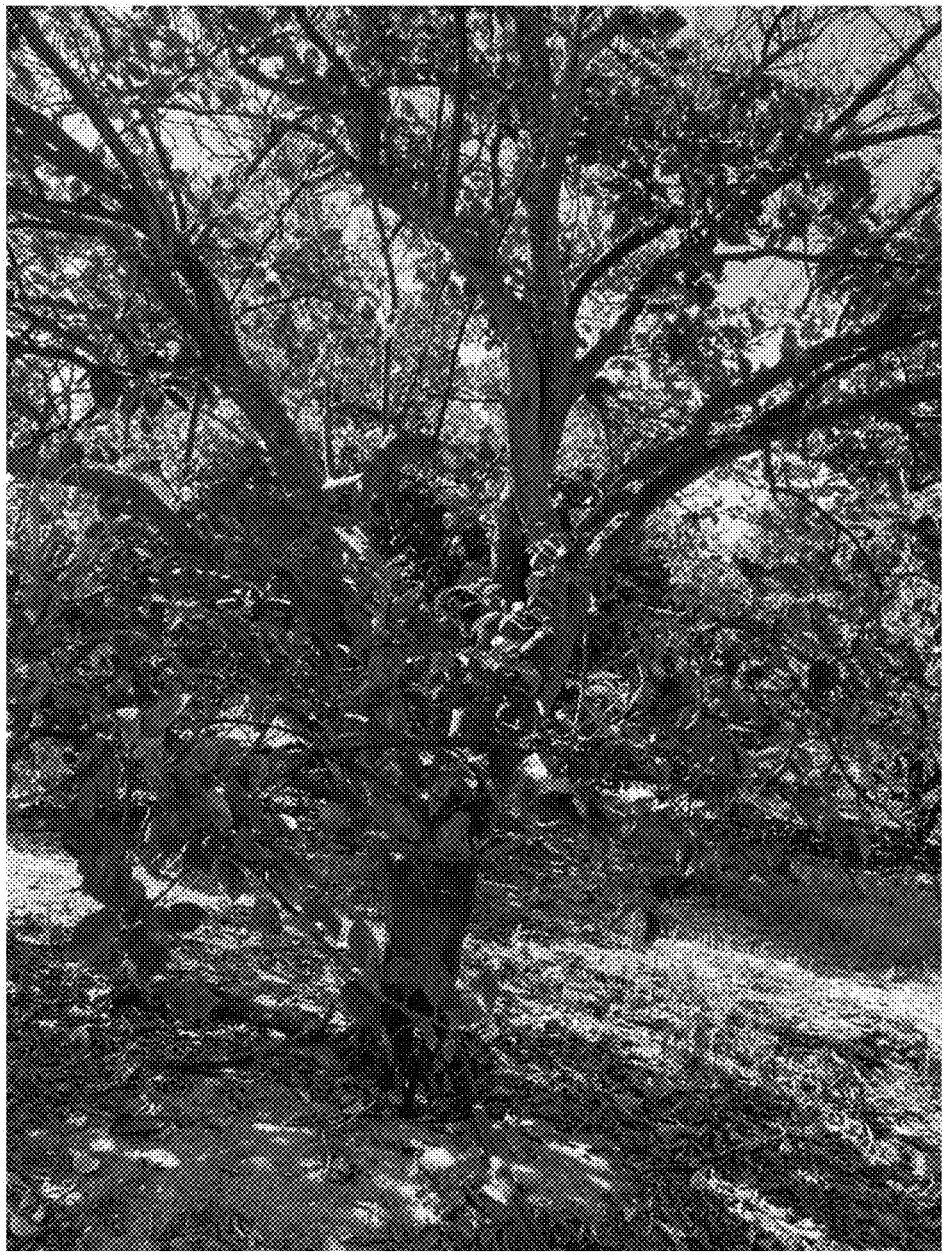
FIG. 1C is a photograph of a tree of the new *Citrus* cultivar showing the overall growth habit, including branching.
Figure 2A:
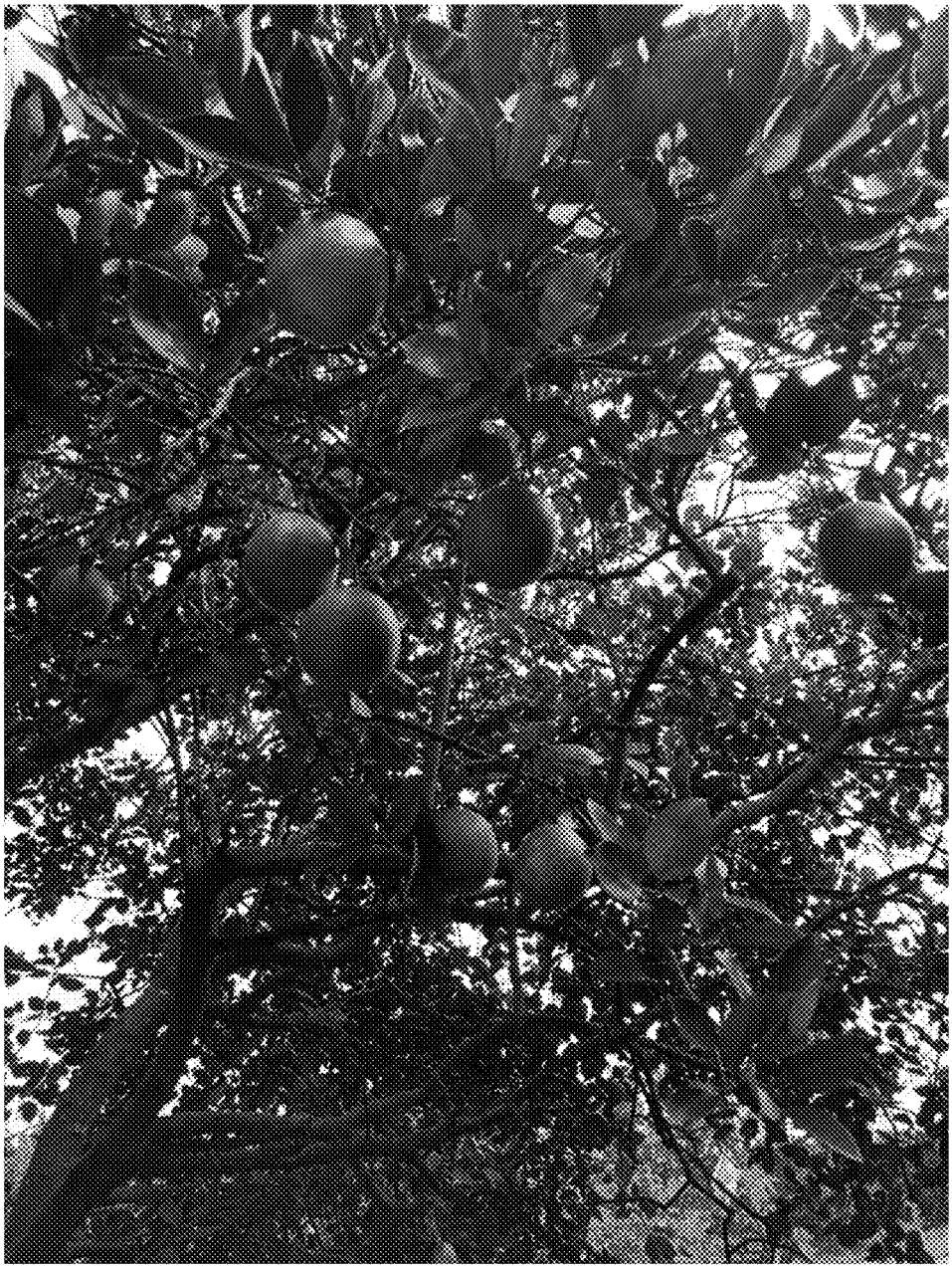
FIG. 2A is a photograph of immature fruit on a tree of the new *Citrus* cultivar.
Figure 2B:
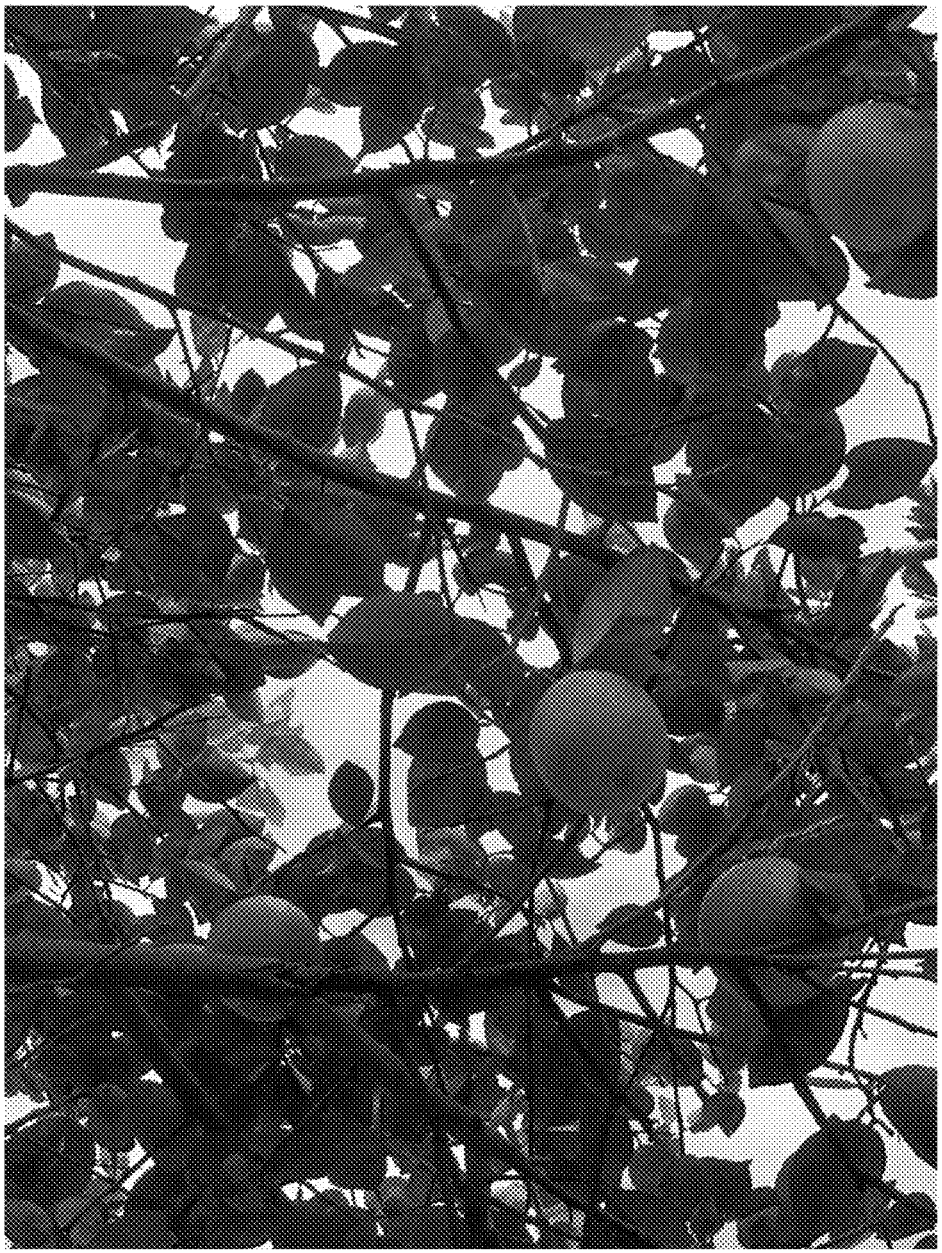
FIG. 2B is a photograph of fruit on a tree of the new *Citrus* cultivar, the fruit being at color break.
Figure 2C:
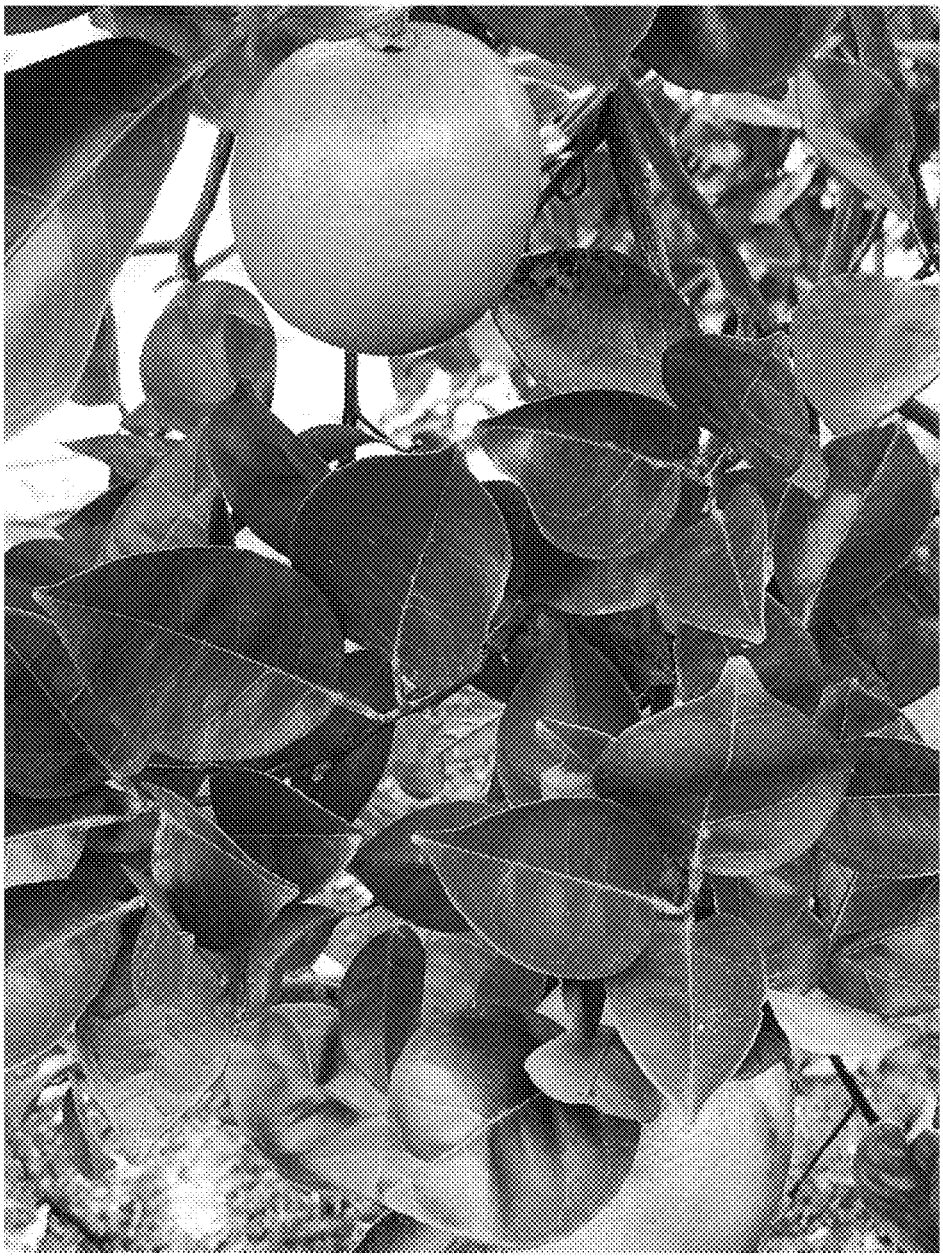
FIG. 2C is a photograph of fruit on a tree of the new *Citrus* cultivar, the fruit being at the earliest point of internal maturity.
Figure 2D:
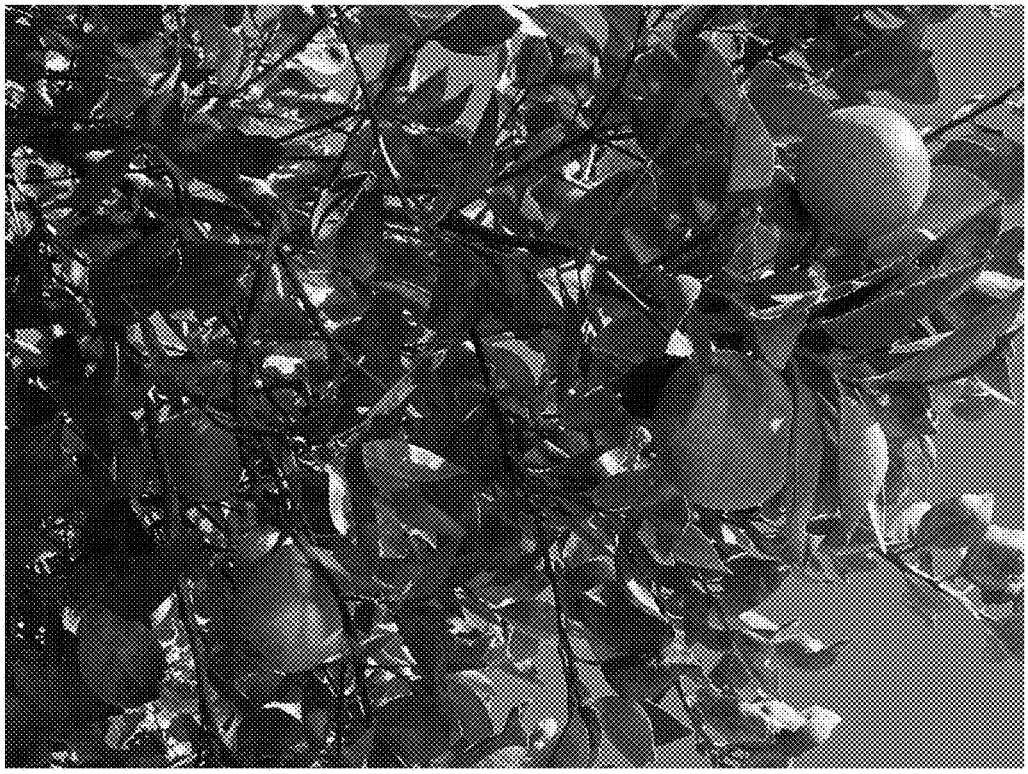
FIG. 2D is a photograph of fruit on a tree of the new *Citrus* cultivar, the fruit being at full maturity.
Figure 3A:
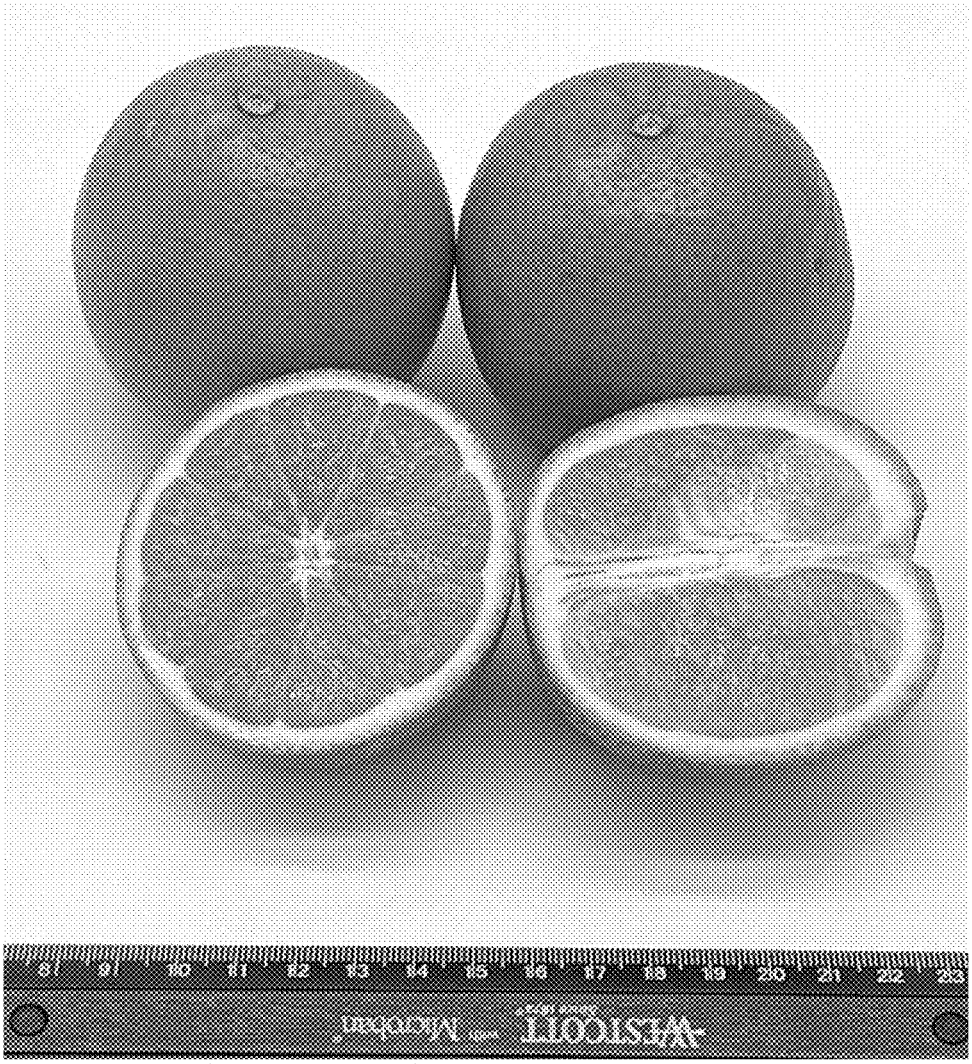
FIG. 3A is a photograph of whole fruit, horizontally cut fruit, and vertically cut fruit at full maturity, showing color and unique tendency to have a rounded to truncated stem and blossom end shape (with a metric ruler shown for reference)
Figure 3B:
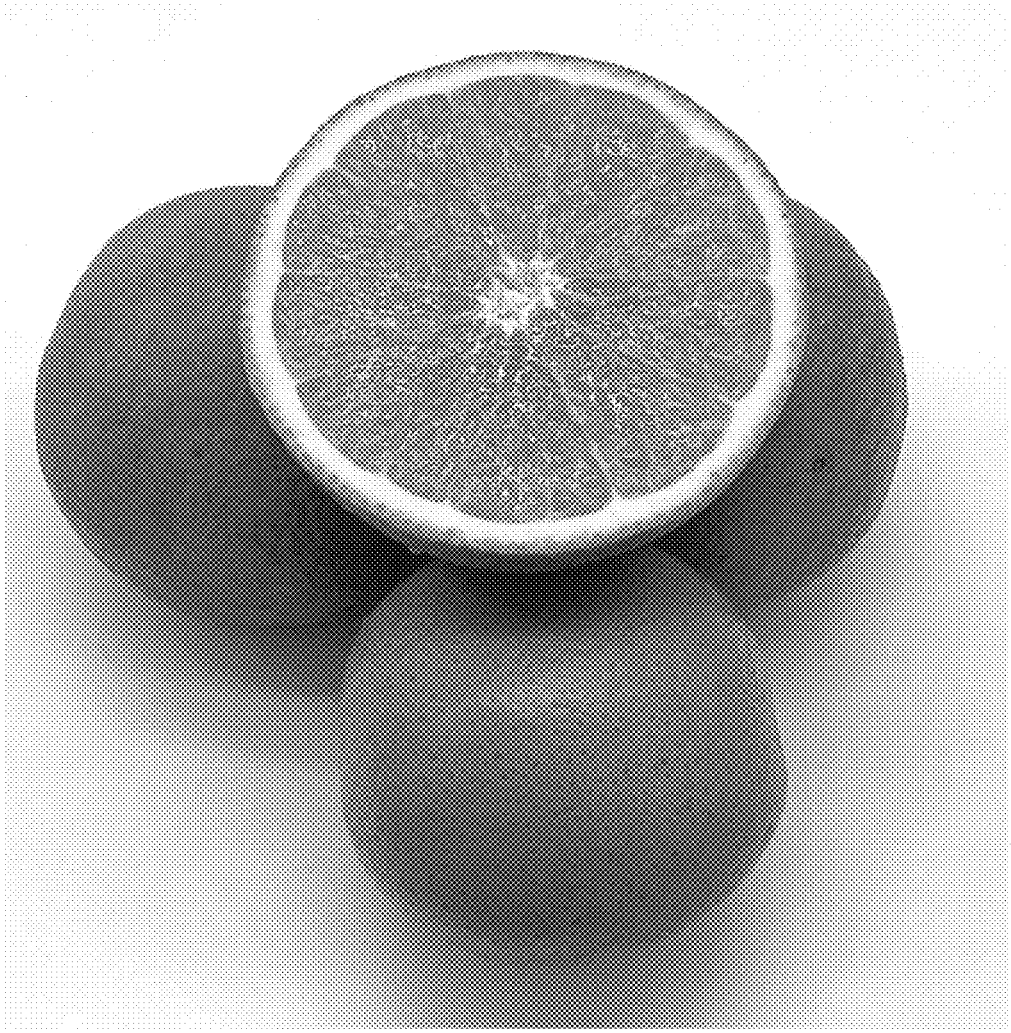
FIG. 3B is a photograph of whole fruit and horizontally cut fruit, showing color and unique tendency to have a rounded to truncated stem and blossom end shape.
Figure 3C:
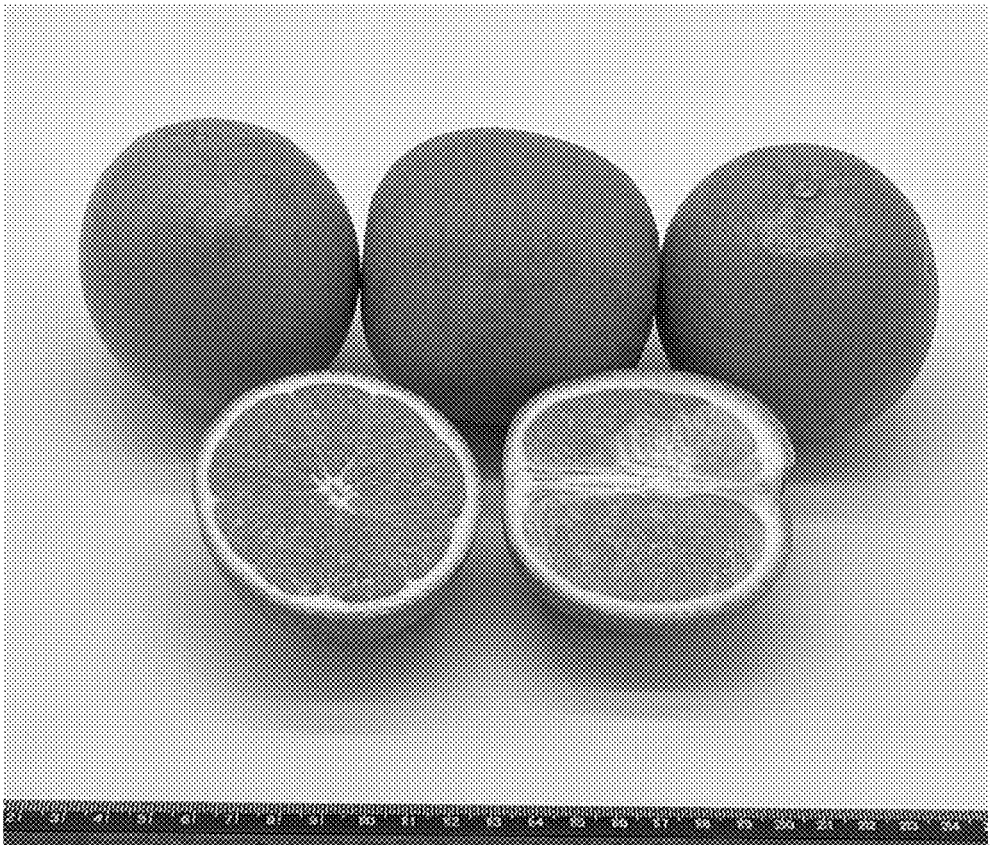
FIG. 3C is a photograph of whole fruit, horizontally cut fruit, and vertically cut fruit at full maturity, showing color and unique tendency to have a rounded to truncated stem and blossom end shape (with a metric ruler shown for reference)
Figure 3D:
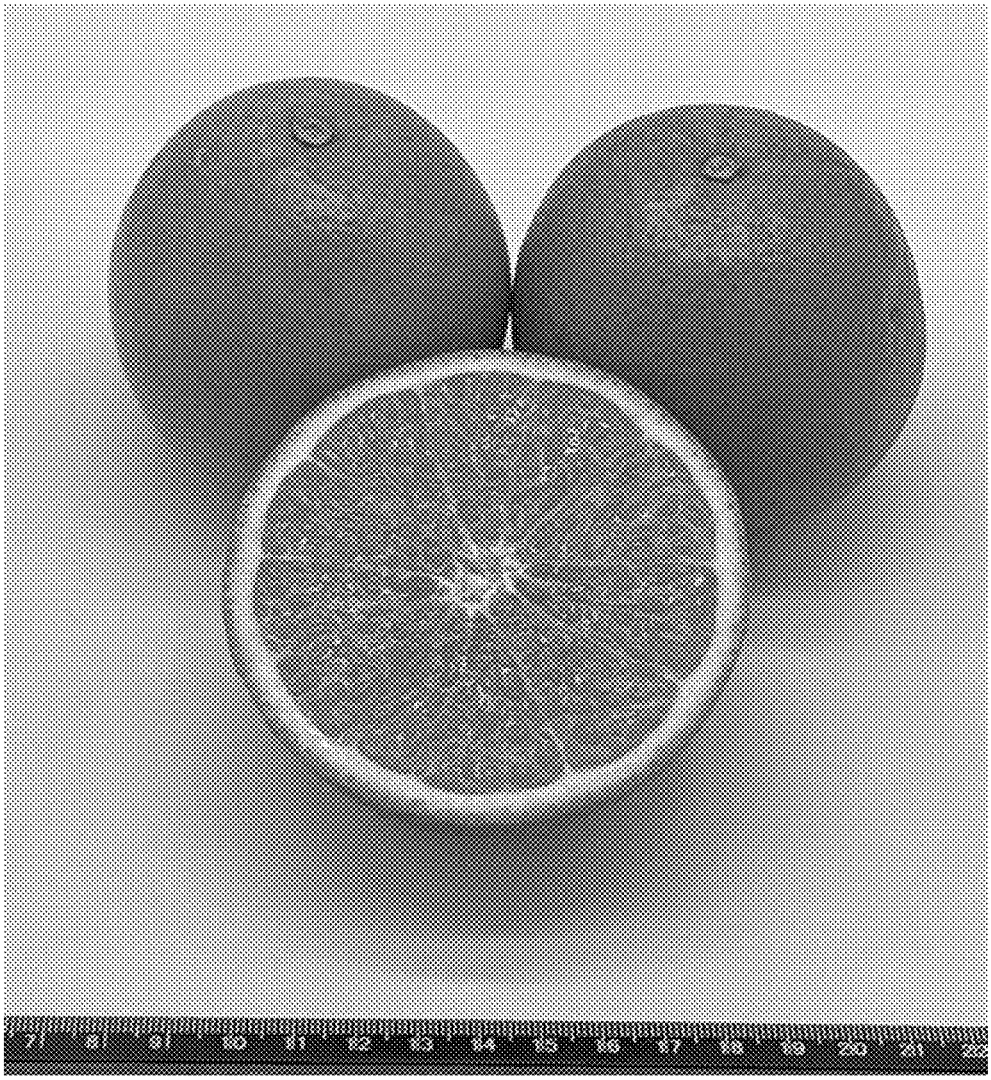
FIG. 3D is a photograph of whole fruit and horizontally cut fruit, showing color and unique tendency to have a rounded to truncated stem and blossom end shape.
Figure 4A:
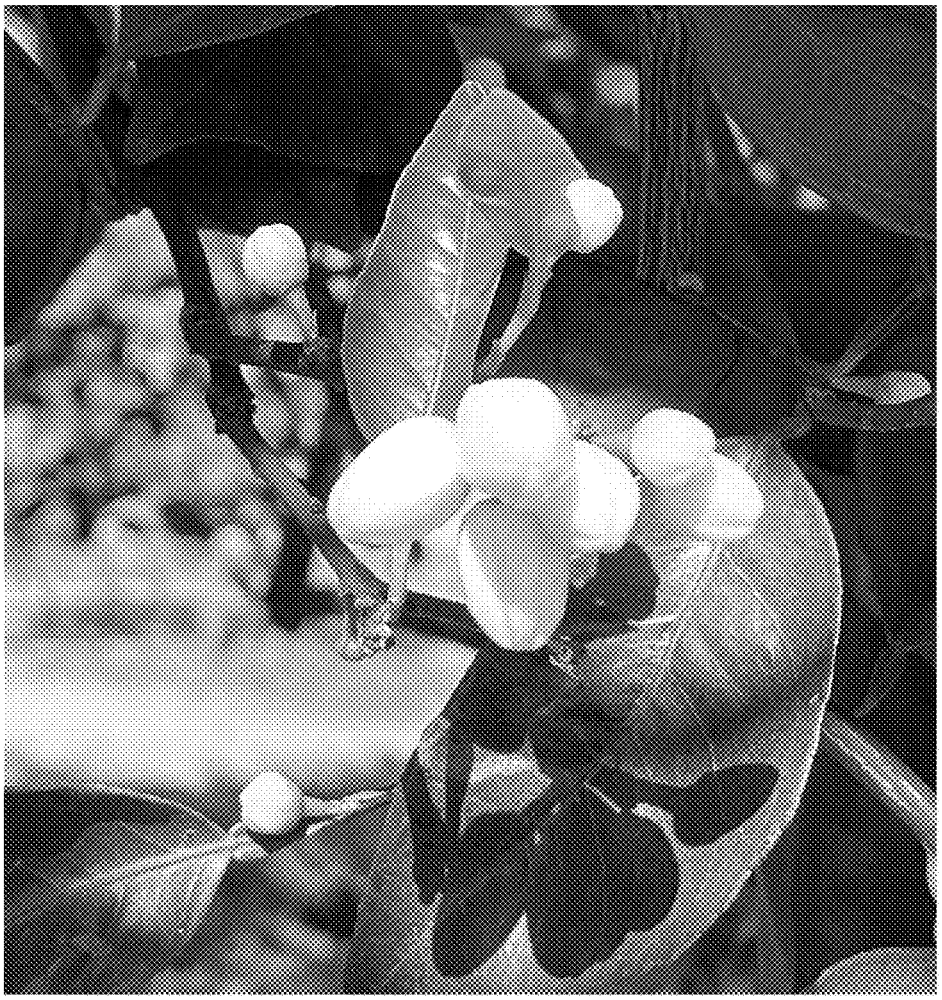
FIG. 4A is a photograph of flower buds on a tree of the new *Citrus* cultivar.
Figure 4B:
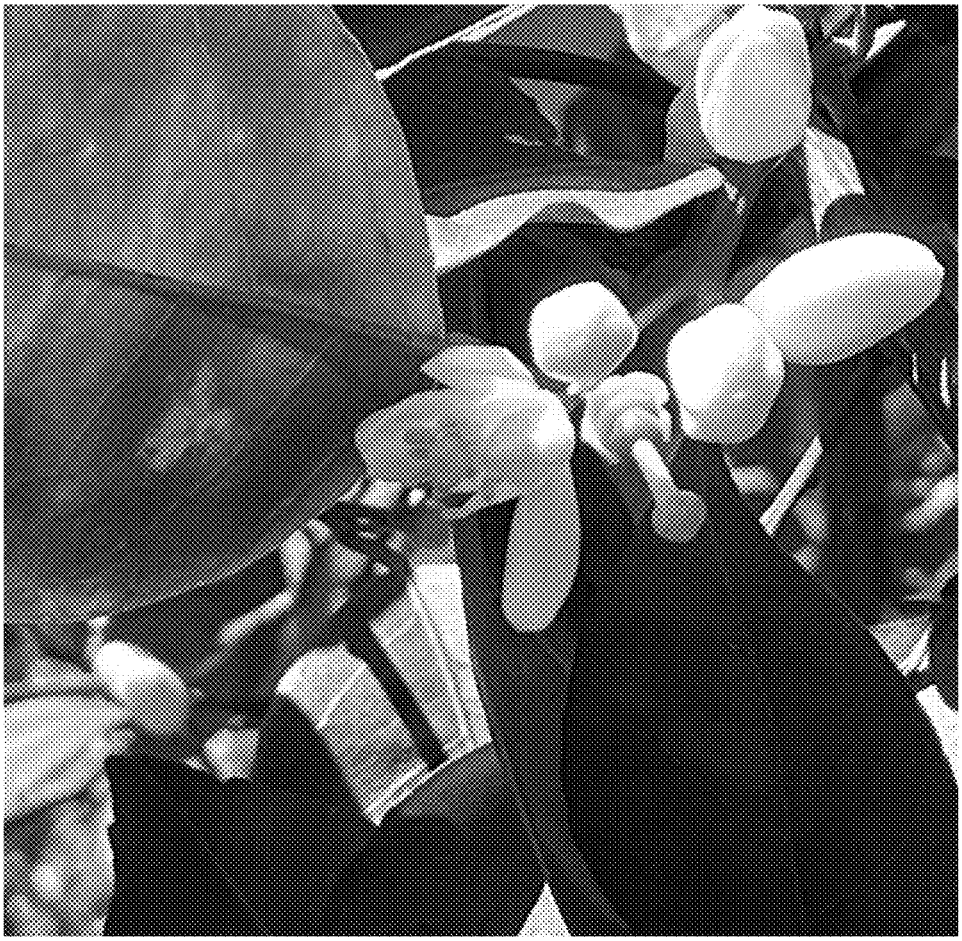
FIG. 4B is a photograph of flowers and flower buds on a tree of the new *Citrus* cultivar.
Figure 4C:
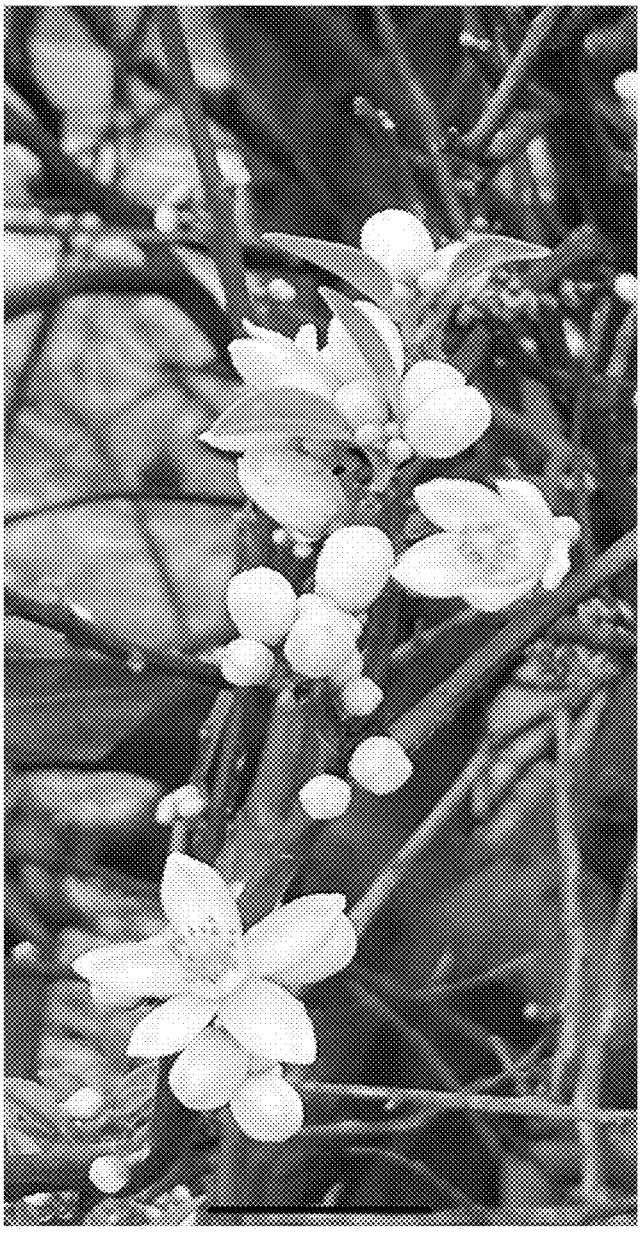
FIG. 4C is a photograph of flowers and flower buds on a tree of the new *Citrus* cultivar.
Figure 4D:
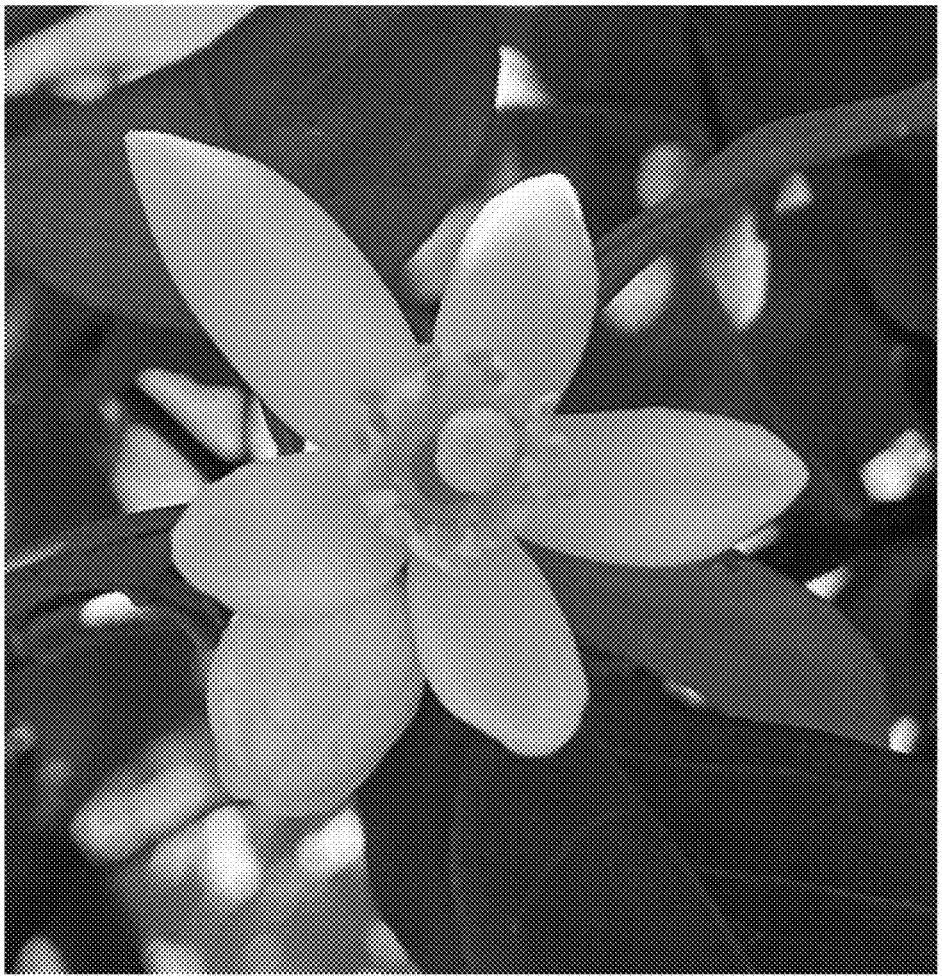
FIG. 4D is a photograph of a flower on a tree of the new *Citrus* cultivar.
Figure 4E:
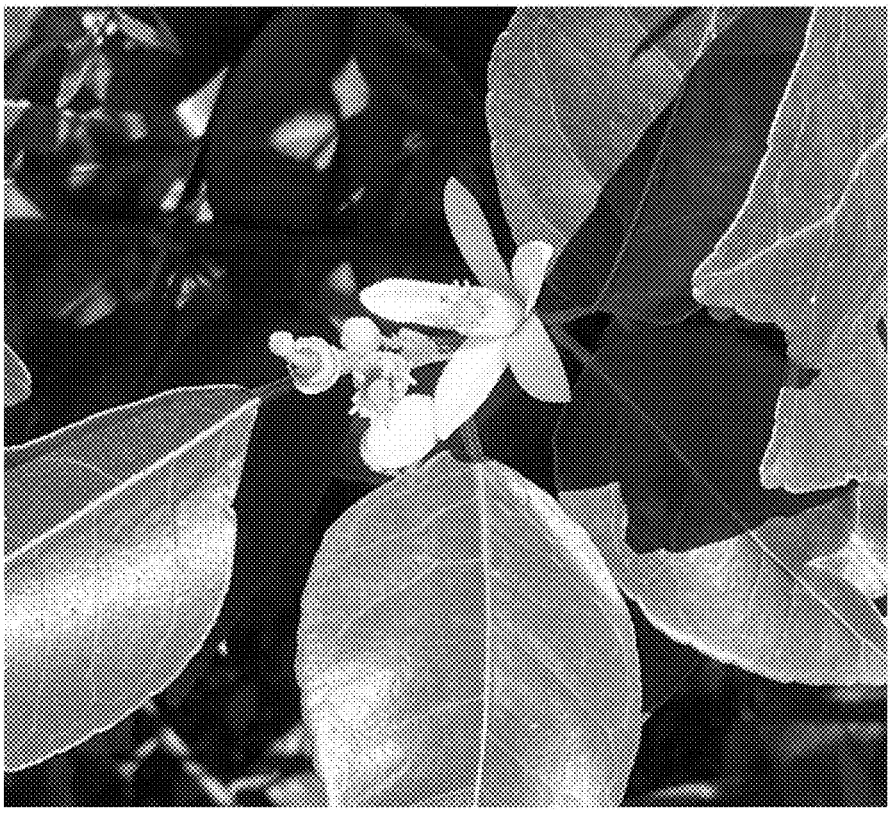
FIG. 4E is a photograph of flowers on a tree of the new *Citrus* cultivar.
Figure 4F:
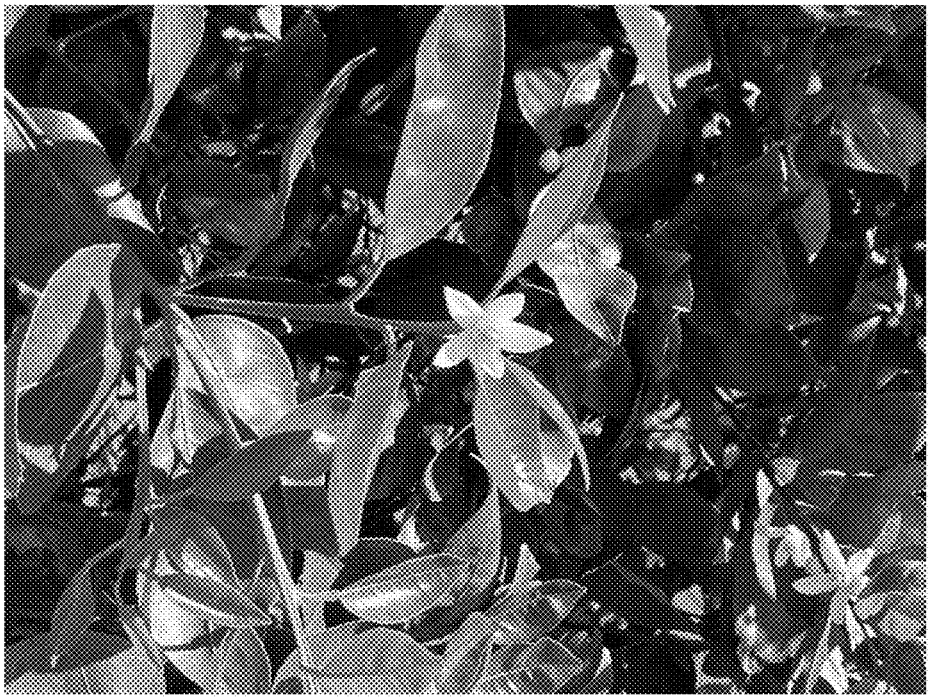
FIG. 4F is a photograph of a flower on a tree of the new *Citrus* cultivar.
Figure 4G:
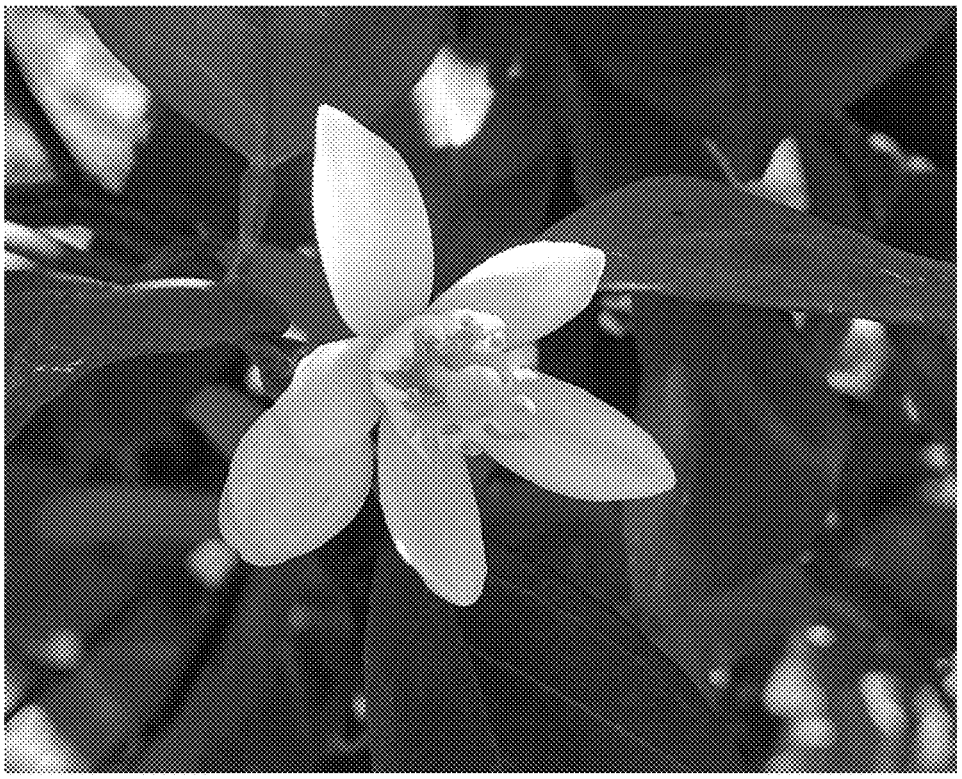
FIG. 4G is a photograph of a flower on a tree of the new *Citrus* cultivar.
Figure 4H:
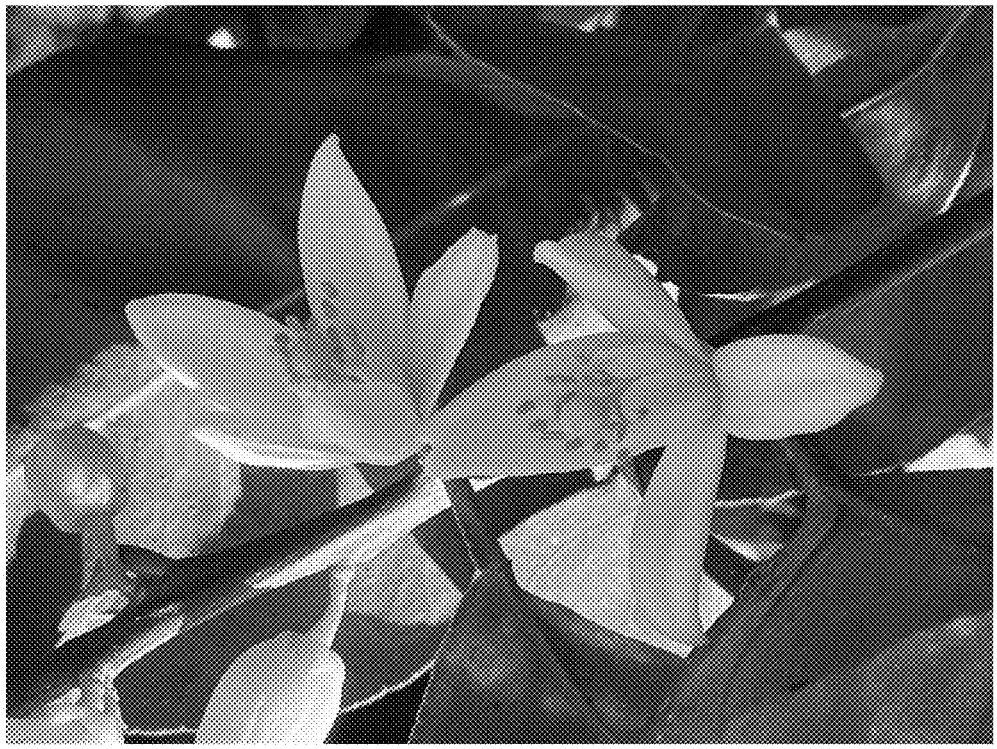
FIG. 4H is a photograph of flowers on a tree of the new *Citrus* cultivar.
Figure 5A:
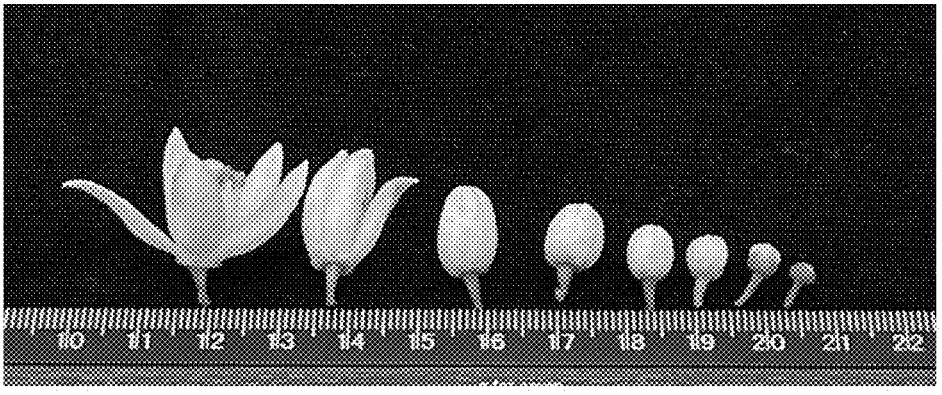
FIG. 5A is a photograph of flowers of the new *Citrus* cultivar, illustrating the size, shape, and color of the flowers in various stages of development (with a metric ruler shown for reference)
Figure 5B:
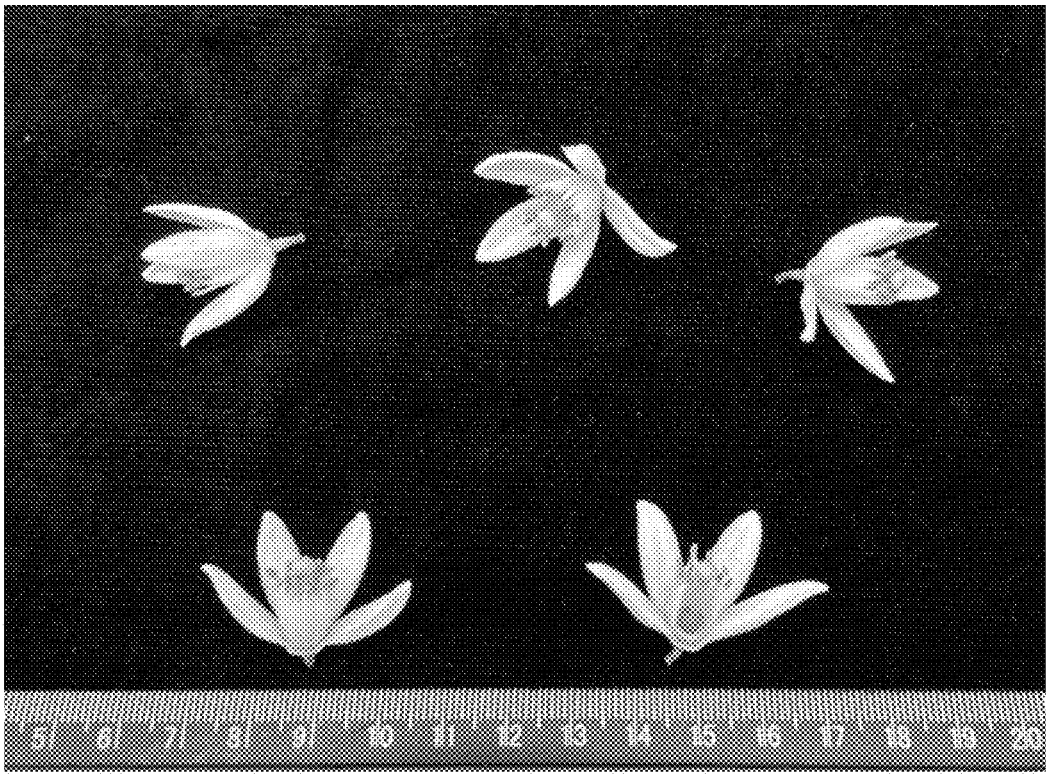
FIG. 5B is a photograph of flowers of the new *Citrus* cultivar (with a metric ruler shown for reference)
Figure 5C:
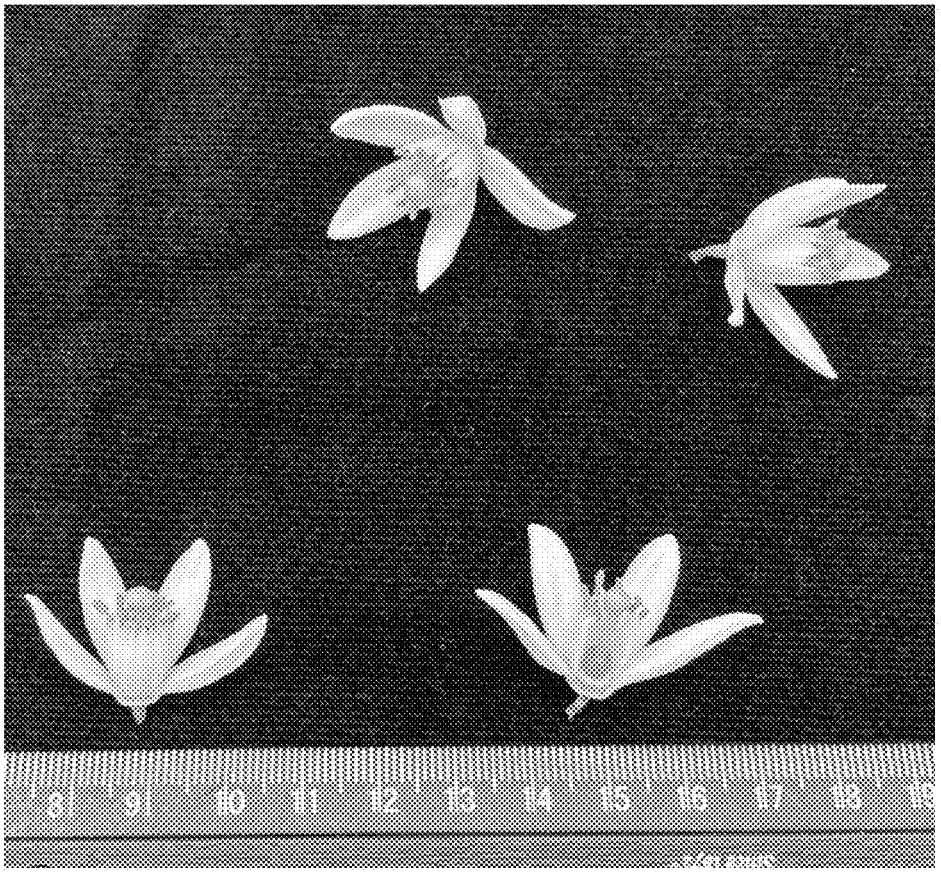
FIG. 5C is a photograph of flowers of the new *Citrus* cultivar (with a metric ruler shown for reference)
Figure 5D:
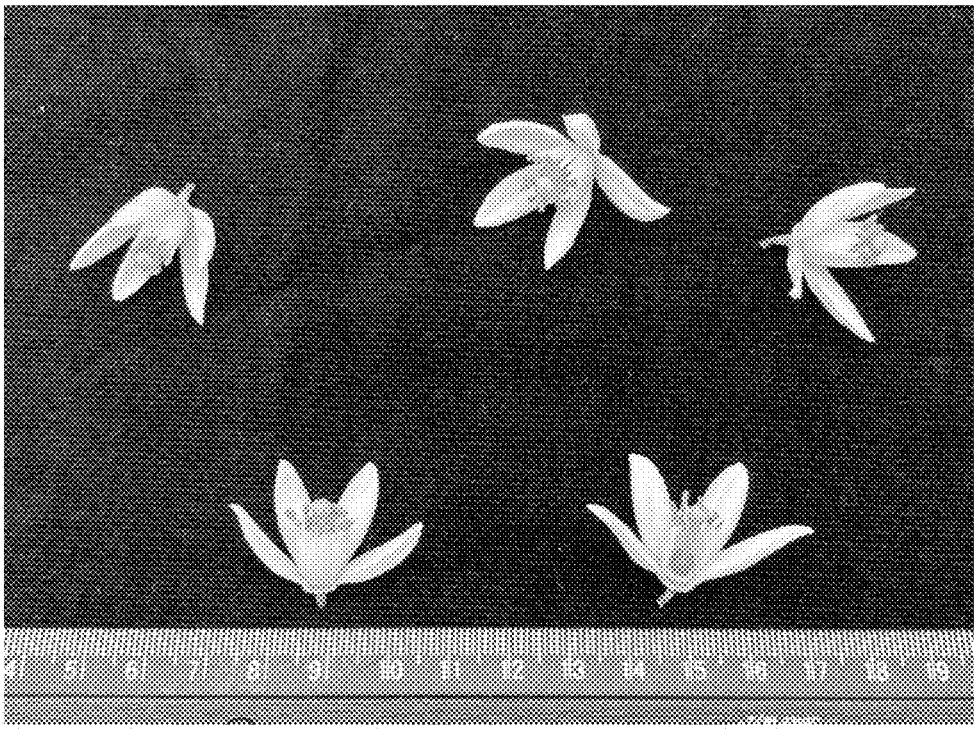
FIG. 5D is a photograph of flowers of the new *Citrus* cultivar (with a metric ruler shown for reference)
Figure 5E:
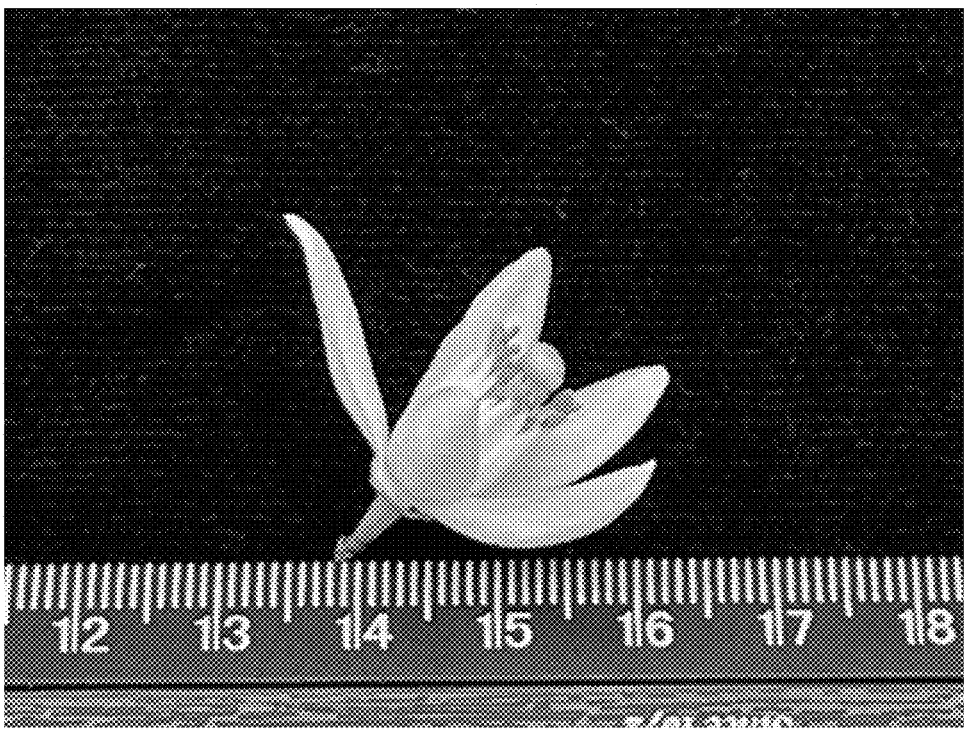
FIG. 5E is a photograph of a flower of the new *Citrus* cultivar (with a metric ruler shown for reference)
Figure 6A:
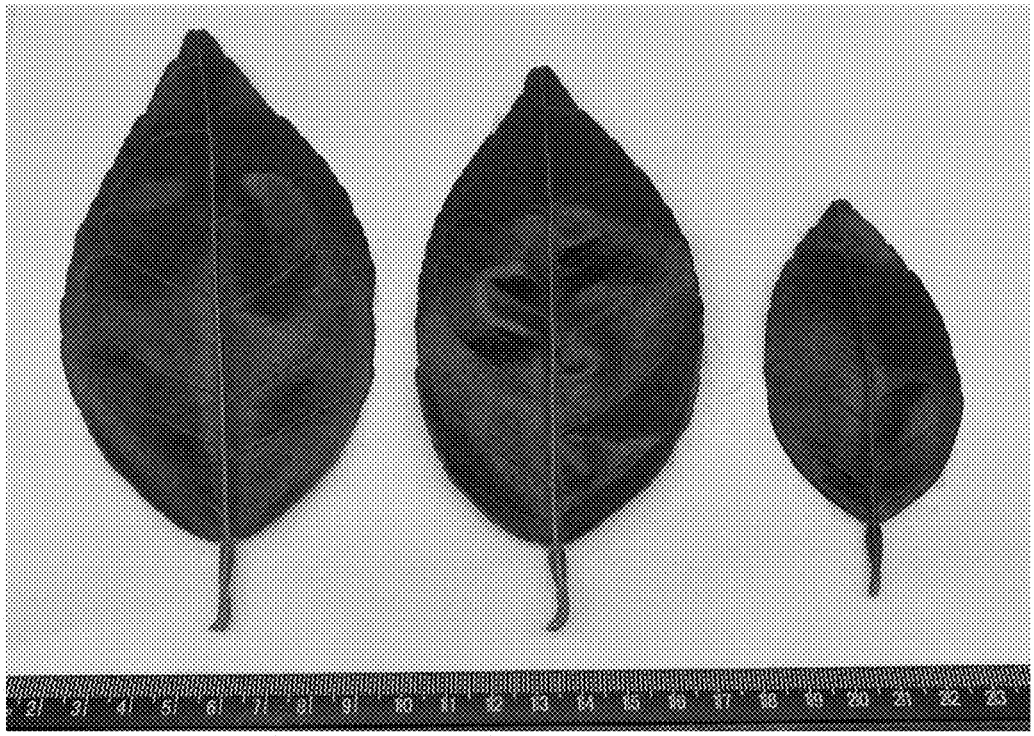
FIG. 6A is a photograph of full expanded leaves of the new *Citrus* cultivar in a range of sizes (with a metric ruler shown for reference)
Figure 6B:
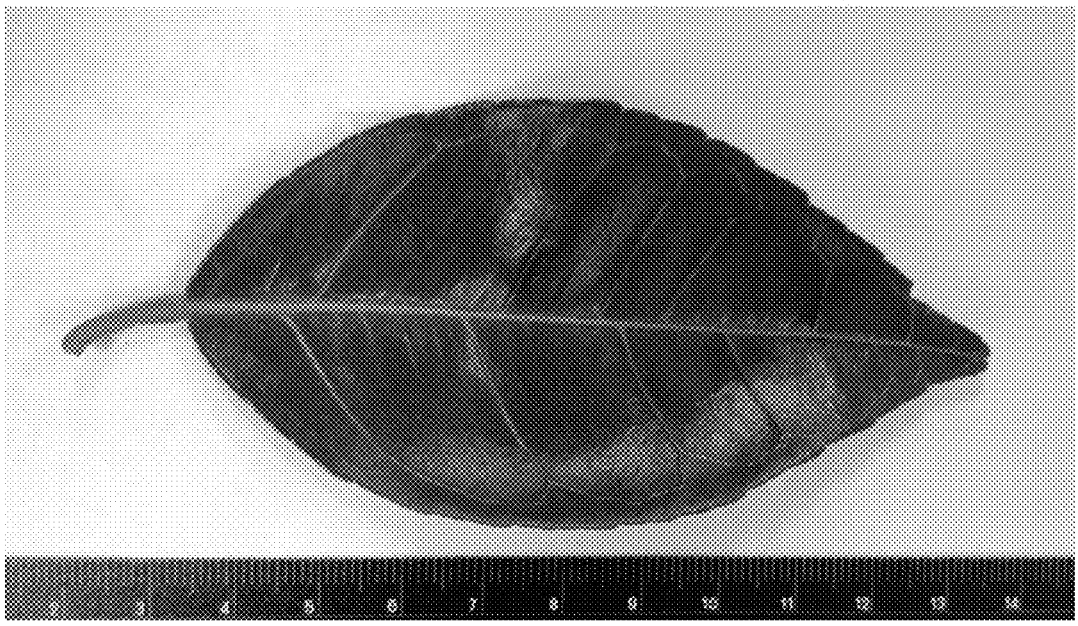
FIG. 6B is a photograph of a fully expanded leaf of the new *Citrus* cultivar (with a metric ruler shown for comparison).

In the following description, color references are made to The Royal Horticultural Society (R.H.S.) Colour Chart published by The Royal Horticultural Society in London (second edition), in association with the Flower Council of Holland, except where general terms of ordinary dictionary significance are used. The juice color score disclosed herein is based on the United States Standards for Grades of Orange Juice published by the United States Department of Agriculture (Jan. 10, 1983).

BOTANICAL DESCRIPTION

Botanical classification:

*Family*.—Rutaceae.

*Botanical name*.—*Citrus* sp. (complex interspecific triploid *Citrus* hybrid).

*Common name*.—*Citrus*.

*Cultivar*.—'UF 1859'.

Parentage: 'LB8-9' (U.S. Plant Pat. No. 21,356; sold commercially as Sugar Belle®) x ('Nova' tangelo (unpatented)+'Succari' sweet orange (*Citrus sinensis* L. Osbeck; unpatented somatic hybrid).

Tree:

*Ploidy*.—Triploid.

*Size*.—Large. Width across row: Approximately 4.3 meters. Width down row: Approximately 3.7 meters.

*Tree height*.—Approximately 4.1 meters.

*Tree canopy diameter*.—Approximately 4.3 meters.

*Density*.—Canopy of HLB-affected tree is moderately dense.

*Tree shape* (*form*).—Oblate shape (obolid).

Trunk:

*Trunk diameter*.—Approximately 20 cm at 30 cm above the ground.

*Trunk texture*.—Relatively smooth.

*Trunk bar color*.—RHS N199 B (Grey-Brown Group).

Branches:

*Branch length.*—3.5 meter on average.

*Branch diameter.*—9.5 cm on average.

*Crotch angle.*—Acute (less than 90°, averaging 80°).

*Branch texture.*—Medium rough.

*Branch color.*—RHS N 199 B (Grey-Brown Group).

Leaves:

*Size (lamina average).*—Length: 120 mm on average. Width: 60 mm on average. Length-to-width ratio: 2 on average. Thickness: Relatively thick.

*Type.*—Simple (unifoliate).

*Shape.*—Elliptical.

*Apex.*—Acute.

*Base.*—Acute.

*Margin.*—Dentated with a split end.

*Surface.*—Upper (adaxial) surface: Smooth and shiny. Lower (abaxial) surface: Medium veins that are pinnately netted.

*Color.*—Upper (adaxial) surface: RHS N 137 A (Green Group). Lower (abaxial) surface: RHS 138 B (Green Group).

*Petiole.*—Shape and attachment: Brevipetiolate; shorter than leaf lamina. Junction between petiole and lamina: Articulate. Shape (petiole wing): Obovate with narrow end at the base. Length: 20 mm on average. Width: 2.5 mm on average. Color: RHS N 137 A (Green Group).

Flowers:

*Type.*—Hermaphrodite.

*Arrangement.*—Flowers borne singly and in clusters of 2-5 flowers each; individual flowers grow from shoot terminals or leaf axils.

*Flower diameter.*—Fully open flowers have an average diameter of 32 mm.

*Flower depth.*—15 mm on average.

*Flower blooming period.*—First bloom: Pinhead bloom usually appears in early February in central Florida, first blossoms open in middle of February. Full bloom: Generally, from late February through middle of March, depending on tree age and season.

*Fragrance.*—Fragrant.

*Flower bud size.*—Length: Approximately 1.8 mm for the initial visible flower bud; approximately 21 mm for the mature flower buds before opened. Diameter: Approximately 1.5 mm in average in the initial visible flower bud; approximately 6.5 mm in the matured bud. Flower bud shape: Initial visible flower bud with round dome shape; mature flower bud with elongated olive shape. Flower bud color: RHS 144 D (yellow-green) for the initial visible flower bud; RHS NN 155B (white) for mature buds.

Reproductive organs:

*Fertility.*—Pollen and ovule are sterile.

*Petals.*—Number (per flower): 5. Petal length: 21 mm on average. Petal width: 6.5 mm on average. Petal shape: Flat spatula shape. Apex shape: Smooth with obtuse angle. Base shape: Obtuse. Petal color: Upper surface: RHS 155 C (White Group). Lower surface: RHS NN 155 AB (White Group). Margin: Smooth.

*Sepal.*—Number (per flower): 5. Shape: Delta shaped with acute angle at apex, although some with flat angle. Length: 3 mm on average. Width: 3.5 mm on average. Apex shape: Acute angle at apex. Margin: Smooth. Color: Upper surface: RHS 158 C (Green White Group). Lower surface: RHS 157 B (Green White Group).

*Pedicel.*—Length: 8 mm on average. Diameter: 1.5 mm on average. Color: RHS 144 A (Yellow Green Group).

*Stamen.*—Number (per flower): 20 on average. Length: 13.5 mm on average.

*Anther.*—Length: 2.5 mm on average. Width: 0.9 mm average. Color: RHS 14A (Yellow Orange Group). Pollen color (general): RHS 13 B (Yellow Group).

*Pistil.*—Number (per flower): 1. Length: 13 mm on average. Color: RHS 153C (Yellow Green Group). Style length: 10.5 mm on average. Style diameter: 2 mm on average. Style color: RHS 144 C (Yellow Green Group). Ovary shape: Oval shape. Ovary diameter: 3.5 mm on average. Ovary color: RHS 143 C (Green Group).

Fruit:

*Size.*—Uniform. Average weight (per individual fruit): 280 grams in average. Length (height): 8.00 cm in average. Diameter: 7.9 cm in average.

*Shape.*—Overall: Spherical, with truncated or flattened stem end and blossom end. Horizontal cross-section: Round. Longitudinal cross-section: Round, with truncated or flattened stem end and blossom end, which gives a blocky appearance. Apex: Rounded to truncate. Base: Rounded to truncate.

*Harvest.*—Date of first pick: Middle of November. Date of last pick: End of January.

*Productivity.*—Small-scale experiments with limited replication have indicated that fruit of the new cultivar 'UF 1859', when harvested at maturity, show minimal losses due to decay or rind breakdown.

*Fruit stem.*—Length: 12 mm on average. Diameter: 5 mm on average. Color: RHS N 199 A (Greyed-Brown Group).

*Rind.*—Adherence: Albedo (mesocarp) to flesh (endocarp) is medium to strong; albedo (mesocarp) to peel is medium. Thickness: Medium (3-4 mm on average). Surface texture: Smooth. Color: Flavedo (epicarp): RHS 23 B (Orange Group). Albedo (mesocarp): RHS 14 C (Yellow-Orange Group). Style end: Closed. Rind oil cell density: 95-100 cell/square cm. Oil gland size: Very small size (0.6 mm on average).

*Flesh.*—Number of segments: 9-10 on average. Segment walls (thickness): Thin to medium soft, but of sufficient strength to maintain integrity as segments are separated. Segment length: 6.9 cm on average. Segment width: 2.7 cm on average.

*Juice.*—Presence: Abundant. Color: RHS 25 B (Yellow-Orange Group). Texture: Soft to medium. Vesicles: Medium thickness. Length: 13 mm on average. Diameter: 3 mm in average. Juice quality (average at full maturity in central Florida, variable by season): Brix: 14.0.Acidity: 0.8%. Ratio (Brix: acidity): 17.5. Juice color score: 37.

*Seeds.*—Presence: Seedless. Fruit parthenocarpy: Weak.

Resistance to disease: No rigorous systematic testing for disease resistance has been conducted until now. The tree was selected from an orchard devasted by Huanglongbing (*Citrus* greening disease) based on its health, indicating of substantial tolerance to this disease, and its ability to produce mostly non-symptomatic fruit.

COMPARISON WITH KNOWN CULTIVARS

The new *Citrus* cultivar 'UF 1859' is a sweet orange-like hybrid, and although the fruit resemble common sweet oranges in several aspects, it can readily be distinguished based on other characteristics. Fruits have much deeper orange-red external pigmentation compared with common oranges that would mature during the same time, such as 'Vernia' (unpatented) or Valquarius™ ('SF14W-62', U.S. Plant Pat. No. 21,535), and the surface of the peel is much smoother. The flesh and juice color are also deeper and more intense than common sweet oranges, and the taste is sweeter with higher Brix than typical oranges, and aroma notes that some describe as "tropical," different from standard sweet orange taste profiles. Fruit shape is unique, with many fruits of 'UF 1859' displaying a characteristic blocky appearance, because of the conspicuous flattening at both the stem and blossom ends of the fruit, whereas the common oranges are rounded. The foliage of 'UF 1859' is distinctly different from common sweet oranges; leaves generally are wider, and because the cultivar is triploid, the leaves tend to be thicker and more deeply green, with a coarse feeling surface.

When compared with the female parent, 'LB8-9', fruit of 'LB8-9' are typically smaller, have a conspicuous neck, and are bell shaped, whereas fruit of the new cultivar '1859' lack an obvious neck and are more spherical. The fruit of 'LB8-9' are seeded following cross-pollination, while fruit of 'UF 1859' are completely seedless under all conditions. When compared with the male parent, ('Nova' tangelo+'Succari' sweet orange somatic hybrid), fruit of the male parent are globose and lack a neck and they usually contain a few to many seeds. Fruit of the new cultivar 'UF 1859' are completely seedless under all conditions. Further, leaves of 'UF 1859' are relatively thicker than those of 'LB8-9' by virtue of the plant's triploid condition, and they lack the typical drooping appearance. The leaves of the male parent are thicker than both 'UF 1859' and those of the female parent as a consequence of its tetraploid condition.

The invention claimed is:

1. A new and distinct *Citrus* plant named 'UF 1859' as illustrated and described herein.

* * * * *